(12) United States Patent
Viebach et al.

(10) Patent No.: US 10,092,171 B2
(45) Date of Patent: Oct. 9, 2018

(54) DEFLECTION MOVEMENT TRANSMISSION DEVICE, ENDOSCOPE BENDING CONTROLLER AND ENDOSCOPE

(71) Applicant: Digital Endoscopy GmbH, Friedberg (DE)

(72) Inventors: Thomas Viebach, Waidhofen (DE); Friedrich Pauker, Diedorf (DE)

(73) Assignee: Digital Endoscopy GmbH, Friedberg (DE)

( * ) Notice: Subject to any disclaimer, the term of this patent is extended or adjusted under 35 U.S.C. 154(b) by 133 days.

(21) Appl. No.: 15/033,074

(22) PCT Filed: Oct. 28, 2014

(86) PCT No.: PCT/EP2014/073065
§ 371 (c)(1),
(2) Date: Apr. 28, 2016

(87) PCT Pub. No.: WO2015/063052
PCT Pub. Date: May 7, 2015

(65) Prior Publication Data
US 2016/0278616 A1 Sep. 29, 2016

(30) Foreign Application Priority Data
Oct. 30, 2013 (DE) .......... 10 2013 222 041

(51) Int. Cl.
*A61B 1/005* (2006.01)
*A61B 1/00* (2006.01)

(52) U.S. Cl.
CPC ........ *A61B 1/0052* (2013.01); *A61B 1/00039* (2013.01); *A61B 1/0057* (2013.01); *A61B 1/00066* (2013.01)

(58) Field of Classification Search
CPC . A61B 1/0052; A61B 1/0057; A61B 1/00066; A61B 1/0051; A61B 1/0053;
(Continued)

(56) References Cited

U.S. PATENT DOCUMENTS 3,549,806 A 12/1970 Wood
3,605,725 A 9/1971 Bentov
(Continued)

FOREIGN PATENT DOCUMENTS

CN 2762381 Y 3/2006
CN 1286664 A 3/2011
(Continued)

OTHER PUBLICATIONS

International Search Report dated Mar. 24, 2015 for International Application No. PCT/EP2014/075902.
(Continued)

*Primary Examiner* — Timothy J Neal
(74) *Attorney, Agent, or Firm* — Knobbe, Martens, Olson & Bear LLP (57) ABSTRACT

The invention refers to a deflection movement transmission device comprising a control element (1) for effecting a deflection movement, the control element (1) having a pivot portion (11; 11') that is supported on a head portion (31; 31') of a base element (3) and is pivotable relative to the head portion (31; 31') of the base element (3) for effecting a deflection movement; at least one movement transmission wire body (2, 2a, 2b) that is articulated to the pivot portion (11; 11') of the control element (1); an elongate transmission guiding body (5) in the longitudinal direction of which the movement transmission wire body (2, 2a, 2b) is guided; and a bendable body (6) to be deflected that is seated at the end of the transmission guiding body (5), opposite to the control element (1), and to which the movement transmission wire
(Continued)

body (2, 2*a*, 2*b*) is mounted in a manner spaced apart from a connection (61) to the transmission guiding body (5).

9 Claims, 9 Drawing Sheets

(58) Field of Classification Search
    CPC .............. A61B 1/0055; A61B 1/0056; A61B
                2219/35417; A61B 2219/35438; A61B
                2034/742; G02B 23/2476; G02B 23/24;
                F16C 1/18; G05B 2219/35417; G05B
                2219/35438
    See application file for complete search history.

(56) References Cited

U.S. PATENT DOCUMENTS

| | | | |
|---|---|---|---|
| 4,241,729 | A | 12/1980 | Aoshiro |
| 4,404,963 | A | 9/1983 | Kohri |
| 4,415,767 | A | 11/1983 | Gill et al. |
| 4,670,009 | A | 6/1987 | Bullock |
| 5,245,133 | A | 9/1993 | DeCarlo et al. |
| 5,569,157 | A | 10/1996 | Nakazawa et al. |
| 5,588,950 | A | 12/1996 | Sano |
| 5,630,419 | A | 5/1997 | Ranalletta |
| 6,383,132 | B1 | 5/2002 | Wimmer |
| 6,547,722 | B1 | 4/2003 | Higuma et al. |
| 6,582,361 | B2 | 6/2003 | Hirano |
| 6,716,160 | B2 | 4/2004 | Mitsumori |
| 7,179,223 | B2 | 2/2007 | Motoki et al. |
| 7,198,599 | B2 | 4/2007 | Goto et al. |
| 7,841,880 | B2 | 11/2010 | Ikeda |
| 2001/0025135 | A1 | 9/2001 | Naito et al. |
| 2002/0040180 | A1 | 4/2002 | Hirano |
| 2002/0115907 | A1 | 8/2002 | Mitsumori |
| 2003/0092965 | A1 | 5/2003 | Konomura |
| 2004/0015050 | A1 | 1/2004 | Goto et al. |
| 2005/0004434 | A1 | 1/2005 | Bob et al. |
| 2006/0116550 | A1 | 6/2006 | Noguchi |
| 2006/0135851 | A1 | 6/2006 | Yamazaki |
| 2006/0199999 | A1 | 9/2006 | Ikeda |
| 2006/0252993 | A1 | 11/2006 | Freed |
| 2007/0156018 | A1 | 7/2007 | Krauter et al. |
| 2007/0221701 | A1 | 9/2007 | Ortiz |
| 2007/0282371 | A1 | 12/2007 | Lee |
| 2009/0209820 | A1 | 8/2009 | Tanaka |
| 2009/0286412 | A1 | 11/2009 | Ikeda |
| 2010/0168560 | A1 | 7/2010 | Hauck et al. |
| 2011/0288372 | A1 | 11/2011 | Petersen |
| 2011/0313252 | A1 | 12/2011 | Lin |
| 2012/0170767 | A1 | 7/2012 | Astrom et al. |
| 2012/0209068 | A1 | 8/2012 | Hosaka |
| 2014/0148646 | A1 | 5/2014 | Inada |
| 2015/0057537 | A1 | 2/2015 | Dillon et al. |
| 2015/0173711 | A1 | 6/2015 | Hiraoka |

FOREIGN PATENT DOCUMENTS

| | | |
|---|---|---|
| CN | 102307510 A | 1/2012 |
| CN | 102401995 A | 4/2012 |
| CN | 102697445 A | 10/2012 |
| CN | 202748535 U | 2/2013 |
| CN | 103153152 A | 6/2013 |
| CN | 103211566 A | 6/2013 |
| DE | 69 05 185 U | 4/1972 |
| DE | 34 46 698 A1 | 7/1985 |
| DE | 196 27 016 C1 | 2/1998 |
| DE | 697 25 670 T2 | 7/2004 |
| DE | 101 48 099 B4 | 6/2006 |
| DE | 10 2009 060 500 | 7/2011 |
| DE | 102010034623 | 2/2012 |
| DE | 10 2012 009332 | 11/2013 |
| EP | 0 028 396 B1 | 4/1981 |
| EP | 0055394 | 7/1982 |
| EP | 1475031 | 11/2004 |
| EP | 1 759 626 A2 | 3/2007 |
| ES | 2 356 497 | 4/2011 |
| JP | S 48 27116 | 8/1973 |
| JP | S 61 118713 | 6/1986 |
| JP | S 62 227312 | 10/1987 |
| JP | H 06254049 | 9/1994 |
| JP | 10-225439 | 8/1998 |
| JP | H11 244225 | 9/1999 |
| JP | A-2001-061772 | 3/2001 |
| JP | 2001510695 | 8/2001 |
| JP | 2002-160691 | 6/2002 |
| JP | 2002 291699 | 10/2002 |
| JP | 2003 190085 A | 7/2003 |
| JP | 2005 304 586 A | 11/2005 |
| JP | 2007 111541 A | 5/2007 |
| JP | 2007313047 | 12/2007 |
| JP | 2009 505688 A | 2/2009 |
| JP | 2009 530051 A | 8/2009 |
| JP | 2009 201762 | 9/2009 |
| JP | 2012 245058 A | 12/2012 |
| WO | WO 00/13569 A1 | 3/2000 |
| WO | WO 00/33727 | 6/2000 |
| WO | WO 2005/094665 A2 | 10/2005 |
| WO | WO2008056642 A1 | 5/2008 |
| WO | WO 2009/008596 | 1/2009 |
| WO | WO 2011/108157 A1 | 9/2011 |
| WO | WO 2011/114772 A1 | 9/2011 |
| WO | WO 2013/129204 | 9/2013 |

OTHER PUBLICATIONS

Mar. 2, 2015 Int'l Search Report from related PCT App. No. PCT/EP2014/077938 (3 pgs).
Mar. 24, 2015 Int'l Search Report from related PCT App. No. PCT/EP2015/051252 (4 pgs).
Apr. 30, 2015 Int'l Search Report from related PCT App. No. PCT/EP2015/051245 (6 pgs).
Anonymous: "Products I BMP-TAPPI", , Jun. 30, 2013 (Jun. 30, 2016), XP055394249, Gefunden im Internet: URL:https://web.archive.org/web/20130630082009/https ://www.bmp-tappi.com:80/products [gefunden am Jul. 27, 2017].
Anonymous: "10. Tappo per innesti rapidi femmina", , Jun. 22, 2013 (Jun. 22, 2013), XP055394266, Gefunden im Internet: U RL :https ://web.arch ive.o rglwebl 201 306221 61 7 34lhTtpl www. bmp-tappi. it:80/po rtfol io_item/tappo-per-i n nesti-rapidifemmina [gefunden am Jul. 27, 2017].
Search Report for Application No. 2015800056419 in 2 pages (English translation).
Search Report for Application No. 2014800410593 in 2 pages (English translation).
Search Report for Application No. 201480076051 in 2 pages (English translation).
Office Action issued Sep. 4, 2017 in 7 pages for Chinese Application No. 201580005641.9 (English translation).
International Search Report dated Oct. 8, 2014 for International Application No. PCT/EP2014/065587.
International Search Report dated Jan. 13, 2015 for International Application No. PCT/EP2014/073064.
International Search Report dated Jan. 13, 2015 for International Application No. PCT/EP2014/073066.
International Search Report dated Jan. 19, 2015 for International Application No. PCT/EP2014/073065.

DEFLECTION MOVEMENT TRANSMISSION DEVICE, ENDOSCOPE BENDING CONTROLLER AND ENDOSCOPE

CROSS REFERENCE TO RELATED APPLICATIONS

This application is a U.S. National Phase of PCT International Application No. PCT/EP2014/073065, filed Oct. 28, 2014 and which claims priority benefit of German Patent Application No. 102013222041.1 filed on Oct. 30, 2013. The entirety of each of the above-identified applications is hereby incorporated by reference.

BACKGROUND

Field of the Invention

The present invention relates to a deflection movement transmission device that transmits a deflection movement effected by a control element to a reaction element. Moreover, the present invention relates to an endoscope bending controller and an endoscope.

Description of Related Art

In such a deflection movement transmission device, a pivotal movement of a control element is converted into a deflection movement of a deflection element. Such deflection movement transmission devices can be used in a versatile manner.

One field of application of the deflection movement transmission device is an endoscope in which a bendable end of a catheter, i.e. a so-called deflecting portion, is moved by pivoting of a control element, wherein the movement of the deflecting portion follows exactly the movement of the control element.

In medical examinations with an endoscope, the transmission of a pivotal movement of a control element to a bending movement of the deflecting portion should be as precise as possible.

SUMMARY

The object of the present invention is to provide an improved deflection movement transmission device.

It is particularly the object of the present invention to provide a deflection movement transmission device with a particular favorable functionality and simple handling. Moreover, an improved endoscope bending controller and an improved endoscope shall be provided.

According to the invention, this object is achieved by a deflection movement transmission device comprising the features of claim 1. Advantageous developments are subject of the dependent claims.

Hence, the invention relates to a deflection movement transmission device comprising a control element for effecting a deflection movement, the control element having a pivot portion that is supported on a head portion of a base element and is relative to the head portion of the base element for effecting a deflection movement; at least one movement transmission wire body articulated at the pivot portion of the control element; an elongate transmission guiding body in the longitudinal direction of which the movement transmission wire body is guided; and a bendable body to be deflected that is seated at the end of the transmission guiding body opposite to the control element, and to which the movement transmission wire body is mounted spaced apart from a connection to the transmission guiding body.

This deflection movement transmission device has a control element at one end. A pivotal movement of the control element is transmitted to a bendable body to be deflected provided at the other end of the deflection movement transmission device via movement transmission wire bodies. The pivotal movement of the control element takes place relative to the base element. During the pivotal movement of the control element, the elements involved in the pivotal movement, i.e. the control element and the base element, are in contact with each other. Thus, a support of the control element on the base element is ensured at the beginning of, during and after the pivotal movement of the control element. This guarantees an exactly defined pivotal movement of the control element.

The movement transmission wire body is articulated to a position on the outer circumference of the pivot portion of the control element, said position changing its distance to the head portion of the base element during a pivotal movement of the control element. In this way, the exactly defined pivotal movement of the control element thus also ensures an exactly defined deflection movement of the bendable body to be deflected.

In one variant, the control element can be configured as an actuating lever which, at the pivot portion, has a foot surface facing the base body, the head portion of the base element having a front face facing the control element, at least the foot surface of the pivot portion of the control element and/or the front face of the head portion of the base element being curved such that the foot surface and the front face can be rolled on each other, and the pivot portion of the control element having the articulation point of the movement transmission wire body at its outer side and, with its foot surface, being pivotally seated on the front face of the head portion of the base element.

The foot surface of the pivot portion of the control element and the front face of the head portion of the base element are opposed to each other. During a pivotal movement of the control element, the foot surface of the pivot portion of the control element rolls on the front face of the head portion of the base element, wherein during this rolling movement the foot surface and the front face are at all times in point contact with each other.

For example, the foot surface of the pivot portion of the control element and/or the front face of the head portion of the base element can be curved outwardly.

In another variant, the control element can be configured as an actuating lever which, at the pivot portion, turns into a hollow ball portion which is at least formed as a ball ring portion, wherein the head portion of the base element is spherically formed, and wherein the hollow ball portion has the articulation point of the movement transmission wire body at its outer side and is slidably seated on the spherical head portion on its inner ball surface.

In this variant, the base element forms an inner ball portion, while the control element has a hollow ball portion seated on the inner ball portion. The ball diameters of the inner ball portion and the hollow ball portion are chosen such that a relative movement of the control element to the base element is easily possible, but an exactly defined pivotal movement of the control element to the base element is ensured.

The movement transmission wire body can be equatorially articulated to the pivot portion of the control element.

At the side facing away from the control element, the head portion can be integrally connected to a rod element as the base element, and the rod element can be axially movable in a rod element holder from which the transmission guiding body extends, in order to tension the movement transmission wire body.

The transmission guiding body can extend from the longitudinal axis of the rod element under a predetermined angle at the side of the rod element holder.

A first end of the movement transmission wire body can be articulated to the control element and an opposite second end of the movement transmission wire body can be fixed to the distal end portion of the body to be deflected.

The transmission guiding body can have a hollow space in which the movement transmission wire body is guided.

The transmission guiding body can be a rail member on which the movement transmission wire body is guided.

The control element can be lockable in order to lock a deflected position of the control element.

The control element can be provided as joystick whose deflected position is lockable by a friction brake.

One, two, three, four or more movement transmission wire bodies can be provided, the first ends of which being equally spaced apart from each other and equatorially articulated to the control element, and the opposite second ends of which being fixed to the distal end portion of the body to be deflected in a corresponding manner equally spaced apart from each other.

The features of the invention can be suitably combined.

Subsequently, the idea of the invention is explained in detail by means of examples.

DETAILED DESCRIPTION OF THE DRAWINGS

In the following, embodiments of the present invention are described in detail by means of the drawings.

First Embodiment

First of all, a first embodiment of the present invention is described in detail by means of FIGS. 1-5.

The first embodiment shows a deflection movement transmission element which is used in an endoscope for an endoscope deflecting control.

In the present embodiment, this deflection movement transmission device consists of a control element 1, several wire bodies 2, a rod element 3 as base element, a rod element holder 4, a catheter tube 5 and a bendable body as deflecting portion 6.

The control element 1 consists of a cylindrical element with a control head 12 with a shaft portion 13 being centrically arranged at the bottom side thereof. The shaft portion 13 has a foot portion 11 at the end opposite to the control head 12. The shaft portion 13 has a constant outer diameter. The foot portion 11 has an outer diameter that increases into the direction opposite to the control head 12.

At the foot portion 11, the control element 1 pivots relative to the rod element 3; therefore, the foot portion 11 of the control element 1 is referred to as pivot portion 11.

At the side opposite to the control head 12, the pivot portion 11 has an end surface formed as foot surface 11A. In the present embodiment, the foot surface 11A is curved outwardly. In other words, the distance, measured in the longitudinal direction of the cylindrical control element 1, between the foot surface 11A and the front face of the control head 12 opposite to the foot, increases from the outer circumference towards the middle. Thus, the foot surface 11A forms a portion of a ball surface with a predetermined radius whose center lies on the imaginary extended axis of the control element 1.

The control element 1 is rotationally symmetrical as it can be seen in FIGS. 1-4. The control element 1 is made of a plastic material but may also be made of metal.

The foot surface 11A of the pivot portion 11 faces a front face 31A of a head portion 31 of the rod element 3, as it is shown in FIGS. 1-4.

The rod element 3 has a longitudinal cylinder 32 which, at its proximal side, turns into the head portion 31. The longitudinal cylinder 32 further has at its distal end portion, a screw end 34 which is designed as an inner square in the present embodiment. Proximally to the square end 34, the rod element 3 has an outer threaded portion 33 at its outer cylinder surface. The rod element 3 is configured rotationally symmetrical. Moreover, the head portion 31, the longitudinal cylinder 32 and the square end 34 are configured as an integral rod element. The longitudinal cylinder 32 of the rod element 3 is formed as a cylinder with a smooth outer surface, except for the threaded portion 33 provided thereon.

In the present embodiment, the front face 31A is also curved outwardly towards the control element 1. In other words, the front face 31A rises from the outer circumference towards the middle in the direction toward the control element 1. The front face 31A forms a portion of a ball surface with a predetermined radius whose center lies on the imaginary extended axis of the rod element 3.

The foot surface 11A and the front face 31A face each other and are in contact with each other. Hence, the pivot portion 11 of the control element 1 is pivotally seated on the front face 31A of the head portion 31 of the rod element 3 with its foot surface 11A.

In a non-pivoted state, the pivot portion 11 of the control element 1 and the head portion 31 of the rod element 3 lie on the same center axis since the control element 1 and the rod element 3 are arranged coaxially to each other in a non-pivoted state. Hence, in the non-pivoted state, the center of the foot surface 11A and the center of the front face 31A touch each other. When the control element 1 is pivoted, i.e.

the pivot portion 11 is inclined relative to the head portion 31 of the rod element 3, the foot surface 11A rolls on the front face 31A.

The control element 1 is thus seated as a joystick on the head portion 31 of the rod element 3.

As it is shown in FIGS. 1-4, the rod element 3 is arranged in the rod element holder 4. The rod element holder 4 is formed as a cylinder element 42 that is configured rotationally symmetrical. The cylinder element 42, in particular, has a hollow space on the side facing toward the control element 1, and a bottom on the side of the rod element holder 4 facing away from the control element 1. The bottom of the rod element holder 4 has a concentric inner channel. In the concentric inner channel, an inner thread 41 is formed at a portion thereof. As it is schematically indicated in FIGS. 1-4, the outer thread 33 of the rod element 3 is seated on the inner thread 41 of the rod element holder 4. By means of a screwing movement the rod element 3 can be concentrically screwed in or out relative to the rod element holder 4. For the purpose of effecting the screwing movement, an appropriate tool is inserted into the square end 34 of the rod element 3. Other relative movement techniques are possible, as it is explained under "Alternatives" at the end of the description.

The cylinder element 42 of the rod element holder 4 has a catheter connecting element 43 at a portion of its outer circumferential side. In the present embodiment, the catheter connecting element 43 extends in an acute angle relative to the cylinder element 42 of the rod element 4, as it becomes apparent from the drawings.

In particular, the catheter connecting element 43 is designed as a round hollow profile which basically constitutes a channel branch from the distal hollow space of the cylinder element 42. The catheter connecting element 43 is formed cylindrically and tapers in the direction away from the cylinder element 42. On the inside, the catheter connecting element 43 has a concentric channel in which the wire bodies 2 are guided. At its distal end, the catheter connecting element 43 has a circular port.

The catheter tube 5 is attached to the circular port of the catheter connecting element 43. In particular, the proximal end 51 of the catheter tube 5 is seated on the port of the catheter connecting element 43.

At its distal end, the catheter tube has a ring 52 incorporated therein. The ring 52 forms the distal end of the catheter tube and the transition to the deflecting portion 6.

The deflecting portion 6 is a bendable body made of an elastic material in a known manner. At its proximal end, the deflecting portion has a deflecting connection 61 at which it is connected to the ring 52 of the catheter tube 5. At the distal end, the deflecting portion has a deflecting cap 62, on which a camera, a laser and/or a camera, etc. are arranged. Further functional units can be integrated at the deflecting cap 62.

Figure 5:
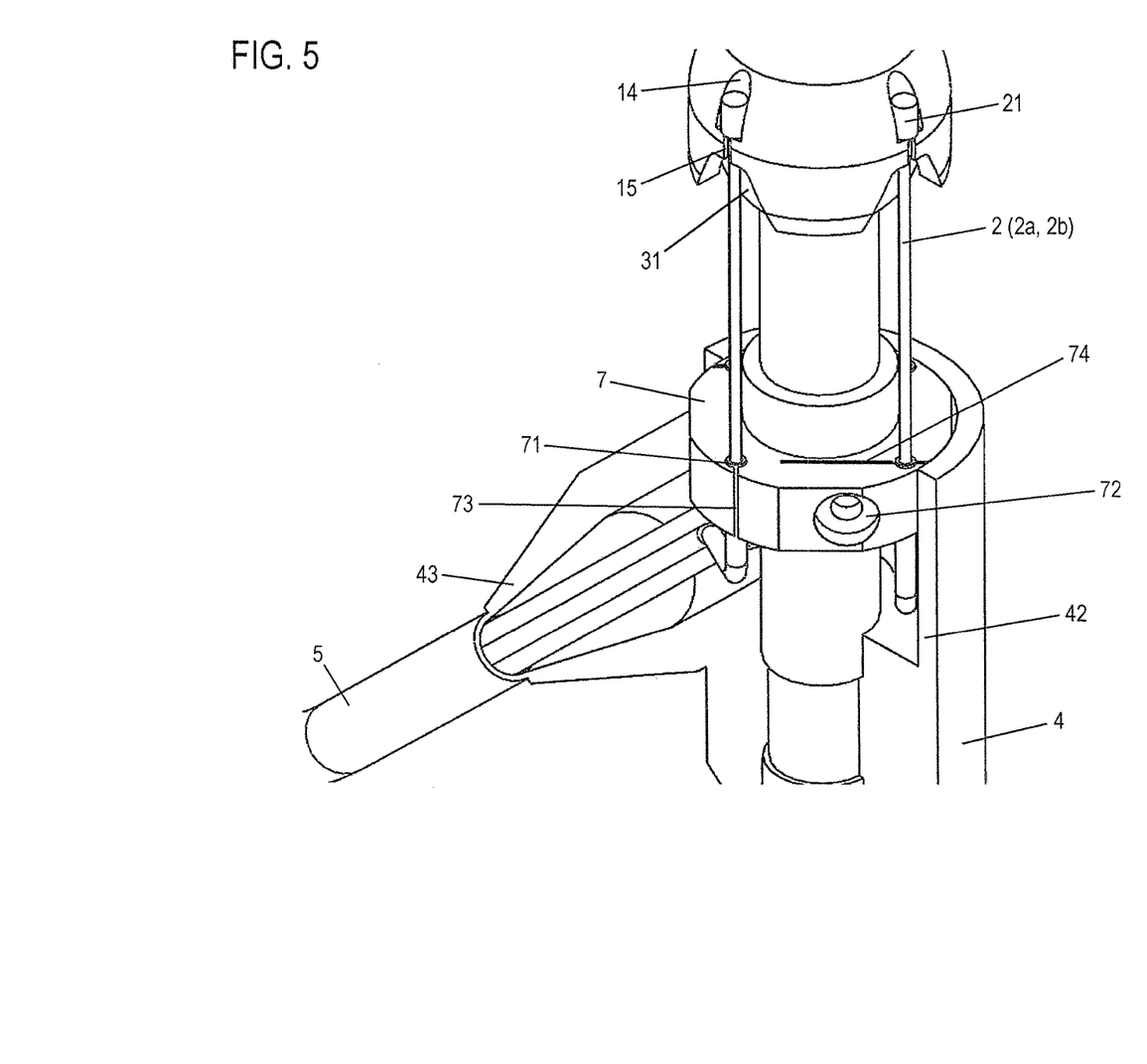
FIG. 5, in a schematic, partial representation in perspective, shows details of the connection of the wire bodies to the control element of the first embodiment and how the wire bodies are guided to the catheter tube.

As it is shown in FIG. 5, several hang-in cavities 14 are provided on the outer circumferential surface of the pivot portion 11 of the control element 1. In the present embodiment, four hang-in cavities 14 are provided on the outer circumferential surface of the pivot portion 11. In particular, the hang-in cavities 14 are recesses formed in the outer circumferential surface of the pivot portion 11 and having a circular cross section and a bottom, the bottom extending approximately perpendicular to an extension direction of the hang-in cavity 14. In other words, the bottom of the hang-in cavity 14 extends approximately parallel to the front face of the control head 12, which is formed at the side of the control element 1 opposite to the foot surface 11A.

When producing the hang-in cavity 14, the pivot portion 11 can be milled such that the hang-in cavity is formed as a laterally open blind hole on the outer circumferential surface of the pivot portion 11. Any other production methods are possible. The outer diameter of the hang-in cavity 14 is chosen in such a way that a barrel nipple 21 of the wire body 2 fits into the hang-in cavity 14. On the bottom of the hang-in cavity 14, i.e. at the distal end of the hang-in cavity 14, a channel 15 is formed as wire body hang-in, the channel extending coaxially to the longitudinal extension of the control element 1 and having a diameter greater than the outer diameter of the wire body 2, but smaller than the outer diameter of the barrel nipple 21 of the wire body 2. In other words, the hang-in cavity 14 and the wire body hang-in 15 are provided, similar to Bowden cable mountings on bicycles, in such a way that a barrel nipple 21 of a wire body 2 can be hung into the same. In a hung-in state of the wire body 2, the barrel nipple forms the proximal end of the wire body 2.

In the present embodiment, four wire bodies 2 are provided, two of which, i.e. the wire body 2a and the wire body 2b, being represented in each of FIGS. 1 to 4. The number of wire bodies 2 is not limited. Only one single wire body 2 may be provided. Two, three, four or more wire bodies may be provided. Should two or more wire bodies 2 be provided, the corresponding hang-in cavities 14 are arranged equally spaced apart from each other on the outer circumferential surface of the pivot portion 11.

Figure 4:
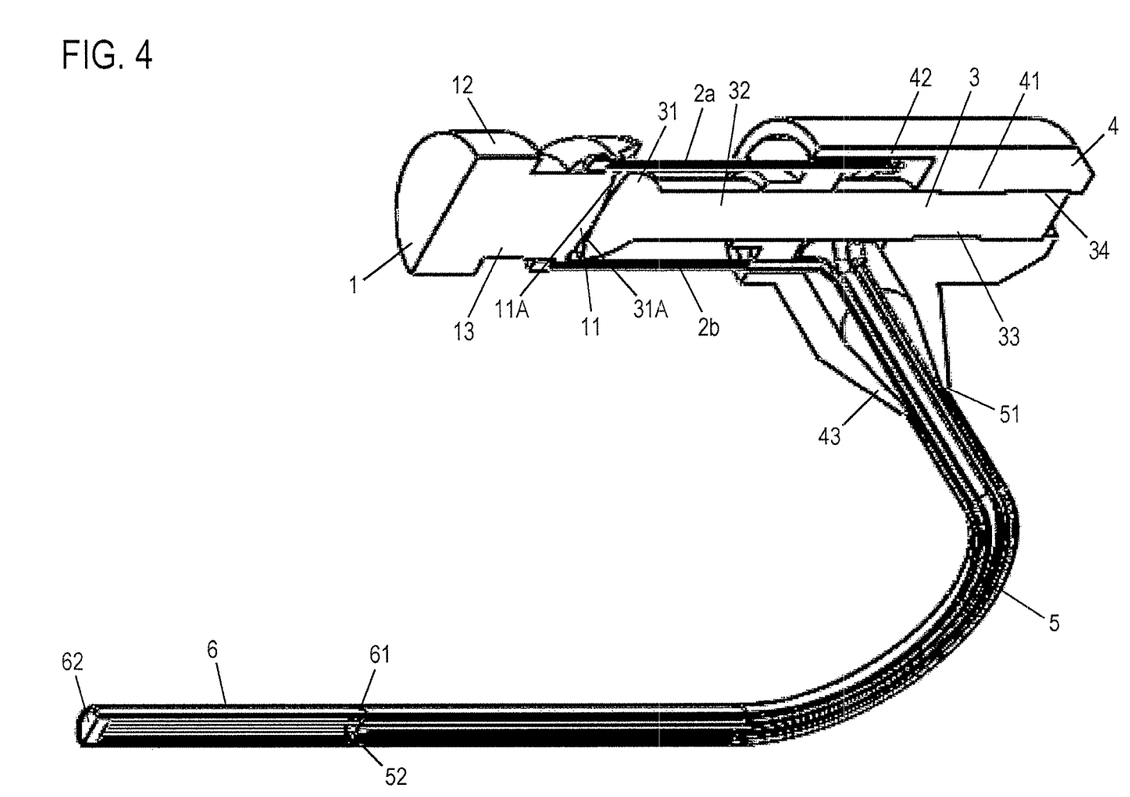
FIG. 4 shows a schematic, cut-open representation in perspective according to FIG. 1.

As it is shown in FIG. 4, the cylinder element 42 has, at its proximal end, i.e. at its end facing the control element 1, an access opening to a hollow space. A wire body guiding ring 7 is inserted into this access opening such that the proximal surface, i.e. the surface of the wire guiding ring 7 facing the control element 1, is aligned with the proximal front face of the cylinder element 42, i.e. the one facing the control element 1. The wire guiding ring 7 is provided with tangential slits 74 in the same number as there are wire bodies 2, as is shown in FIG. 5. Wire guide openings 71 extending coaxially to the center axis of the wire guiding ring 7 are drilled into the slits 74. Incidentally, the center axis of the wire guiding ring 7 is coaxial to the respective axes of the rod element 3 and the cylinder element 42 of the rod element holder 4. More specifically, the distance from each hang-in cavity 14 to the center axis of the control element 1 is exactly the same as the radial distance between the wire guiding bore 71 and the center axis of the wire guiding ring 7. Each wire guiding bore 71 is centered to a corresponding wire body hang-in 15.

The slit end 73 of any tangential slit 74 is located at the outer circumferential surface of the flat wire guiding ring 7, as is shown in FIG. 5. Furthermore, the outer circumferential surface of the flat wire guiding ring 7 is provided with a threaded hole 72 that accommodates a fixing screw by means of which the wire guiding ring 7 is fixed to the cylinder element 42 of the rod element holder 4. Although only one threaded hole 72 for a fixing screw is shown in FIG. 5, also plural threaded holes 72 for a corresponding number of plural fixing screws can be provided on the wire guiding ring 7.

The wire bodies 2 are guided through the catheter tube 5 and through the ring 52 of the catheter tube and are anchored at the deflecting cap 62 of the deflecting portion 6. In particular, the wire bodies 2 are anchored at the deflecting cap 62 in a way such that they are equally spaced apart from each other and are arranged in the same order as at the pivot portion 11.

The ring 52 has openings for the wire bodies 2 in a manner corresponding to the design of the wire guiding ring 7.

The length of each wire body 2 from the fixing point at the deflecting cap 62 to the fixing point at the pivot portion 11 is always the same.

Mode of Operation

Figure 1:
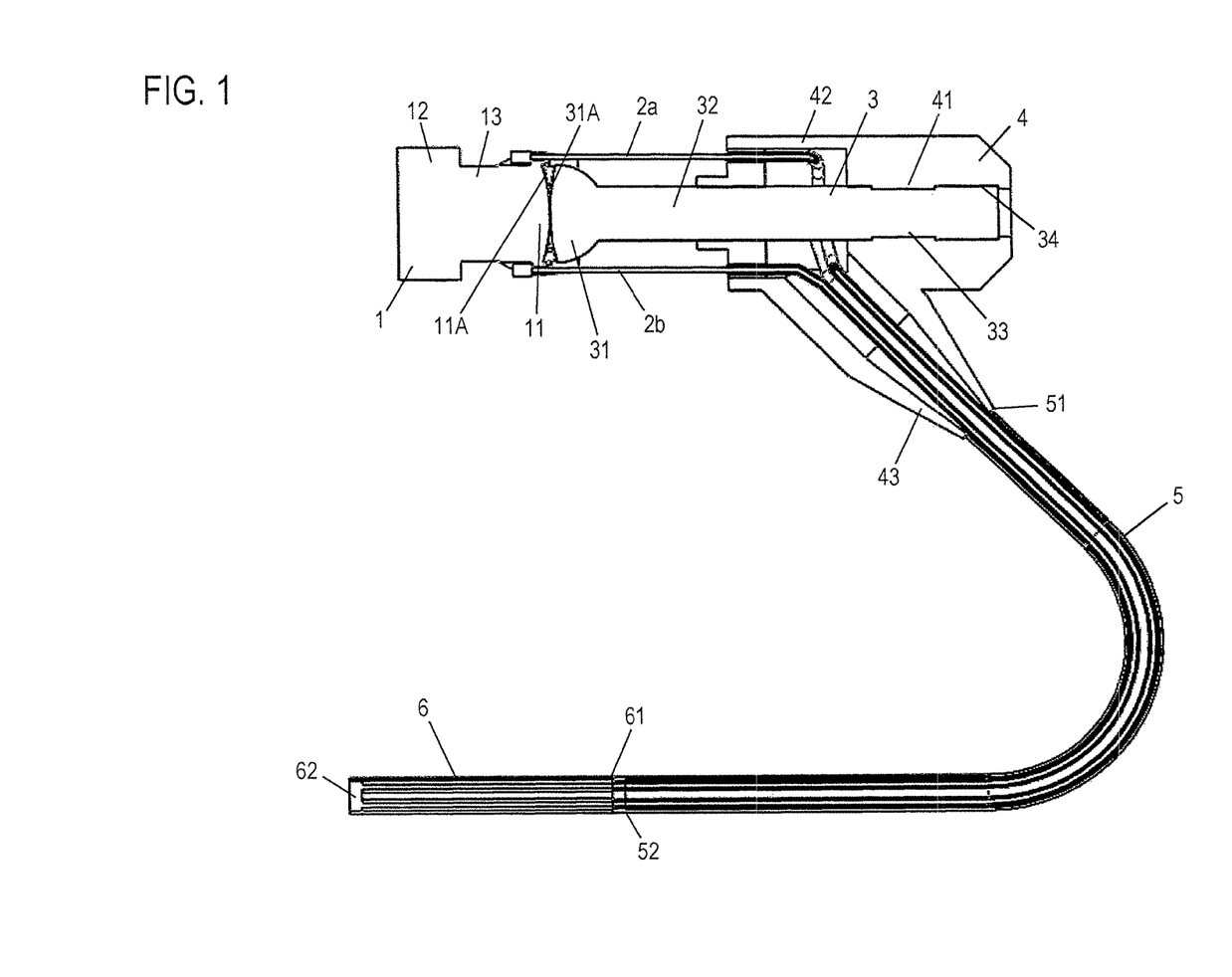
FIG. 1 shows a schematic sectional view of the deflection movement transmission device of a first embodiment in a non-deflected state.

The control element 1 can be operated as a joystick, wherein its pivot portion 11 can be moved in a rolling manner on the head portion 31 of the rod element 3. Thus, when the pivot portion 11 is inclined relative to the head portion 31 of the rod element 3, the foot surface 11A rolls on the front face 31A. Thereby, the ends of the wire bodies 2, arranged at the pivot portion 11, are pulled or pushed relative to the assembly of rod element 3, rod element holder 4 and catheter tube 5.

A pivoting operation of the joystick 1 relative to the rod element 3 in any direction is thereby possible. The direction and the extent of the deflection movement of the joystick 1 relative to the rod element 3 is then transmitted by the wire bodies 2 arranged at the deflecting cap 62 to the deflecting portion 6 designed as bendable body.

Figure 2:
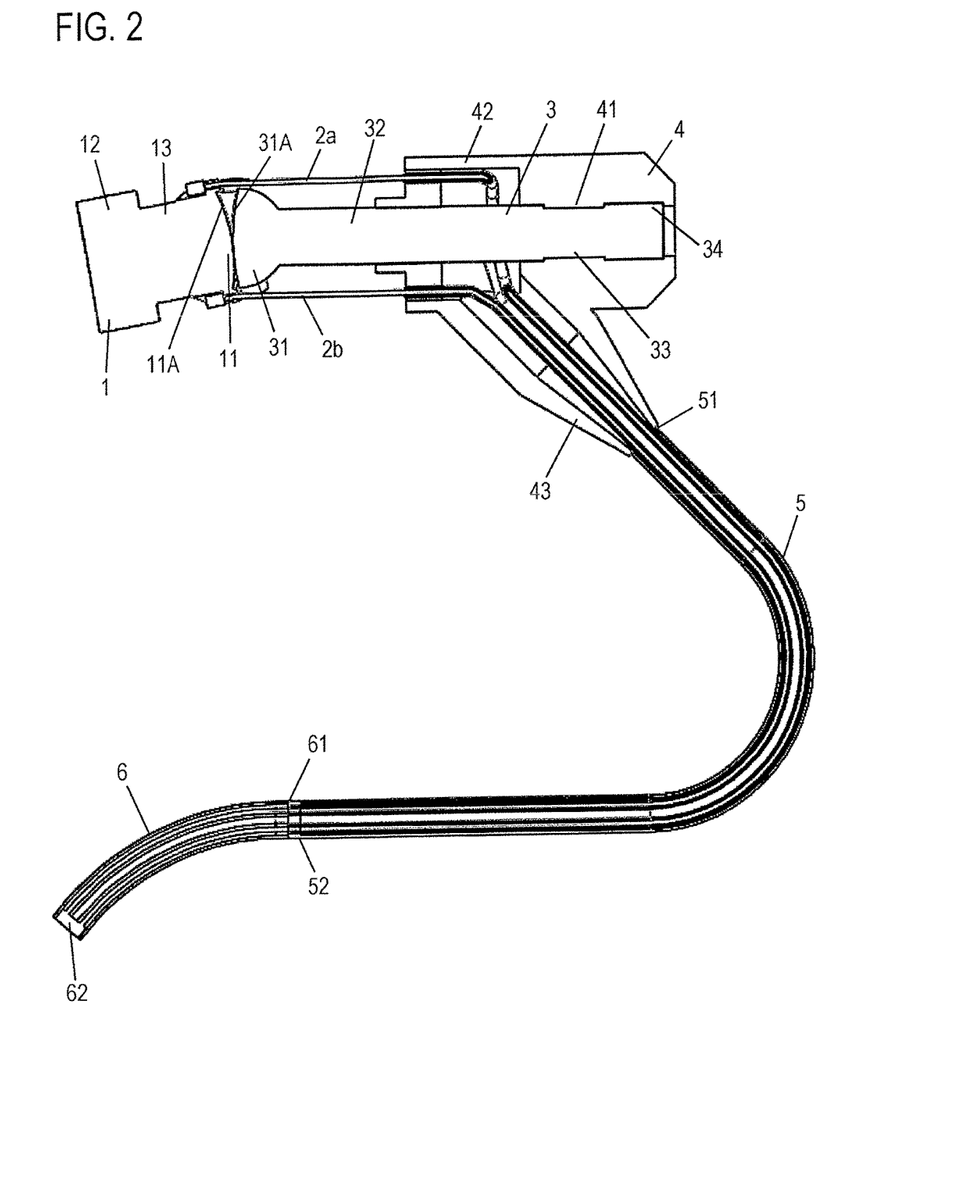
FIG. 2 shows a schematic sectional view of the deflection movement transmission device of the first embodiment when deflected to the left.

In other words, if, as is shown in FIG. 2, the joystick 1 is moved to the left relative to the rod element 3, the right wire body 2a is pulled, whereby in the deflecting portion 6 the right wire body 2a pulls the deflecting cap 62 in a proximal direction. At the same time, the left wire body 2b is pushed, whereby in the deflecting portion 6 the left wire body 2b pushes the deflecting cap 62 in a distal direction. Thus, in FIG. 2, the deflecting portion performs a movement directed to the left.

Figure 3:
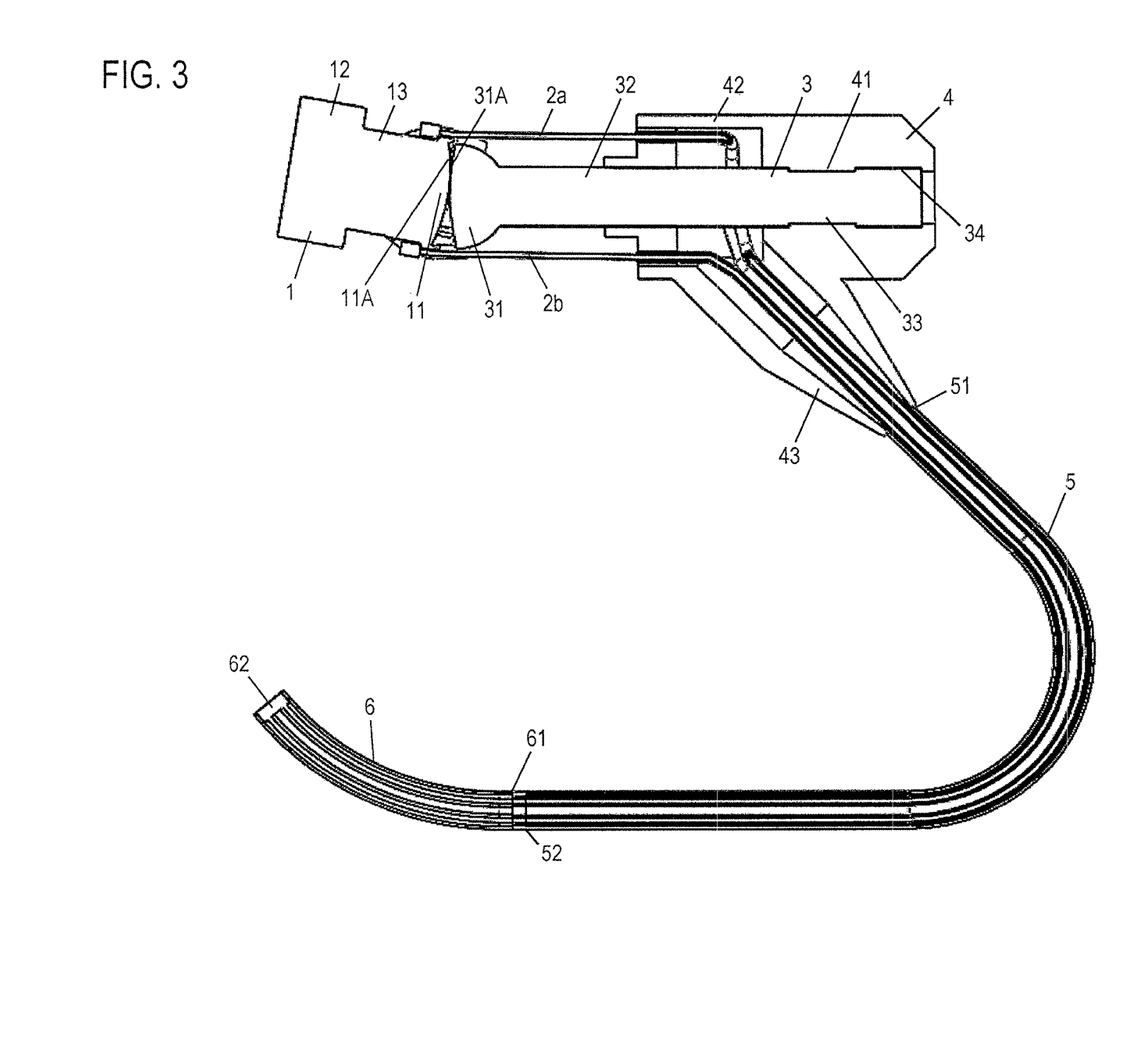
FIG. 3 shows a schematic sectional view of the deflection movement transmission device of the first embodiment when deflected to the right.

If the joystick 1 is moved to the right relative to the rod element 3, the deflecting portion performs a movement directed to the right, as is the case in FIG. 3.

Second Embodiment

Subsequently, a second embodiment of the present invention is described in detail by means of FIGS. 6-9.

Also in the present embodiment, the deflection movement transmission device consists of a control element 1, several wire bodies 2, a rod element 3, a rod element holder 4, a catheter tube 5 and a bendable body as deflecting portion 6.

Figure 6:
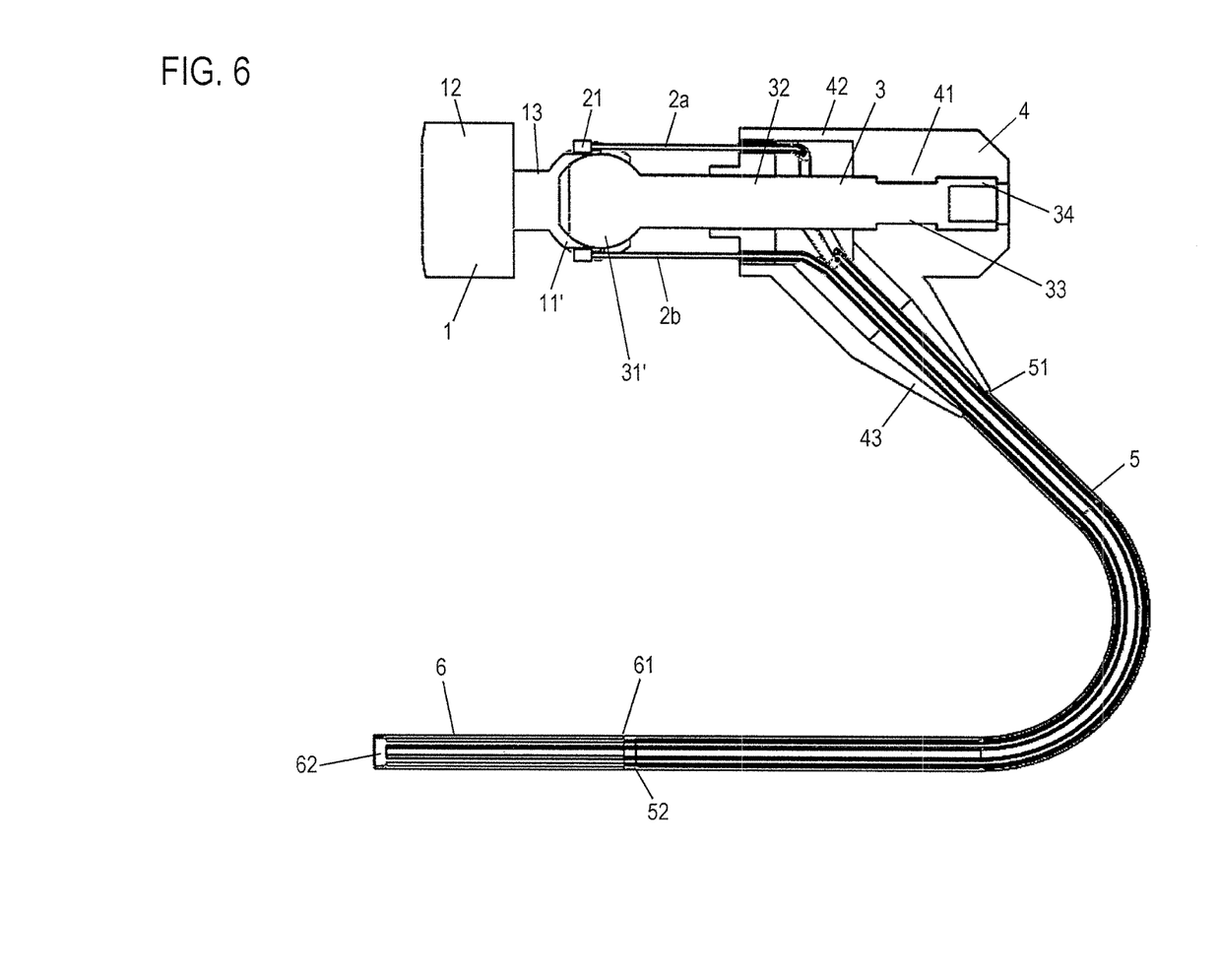
FIG. 6 shows a schematic sectional view of the deflection movement transmission device of a second embodiment in a non-deflected state.
Figure 7:
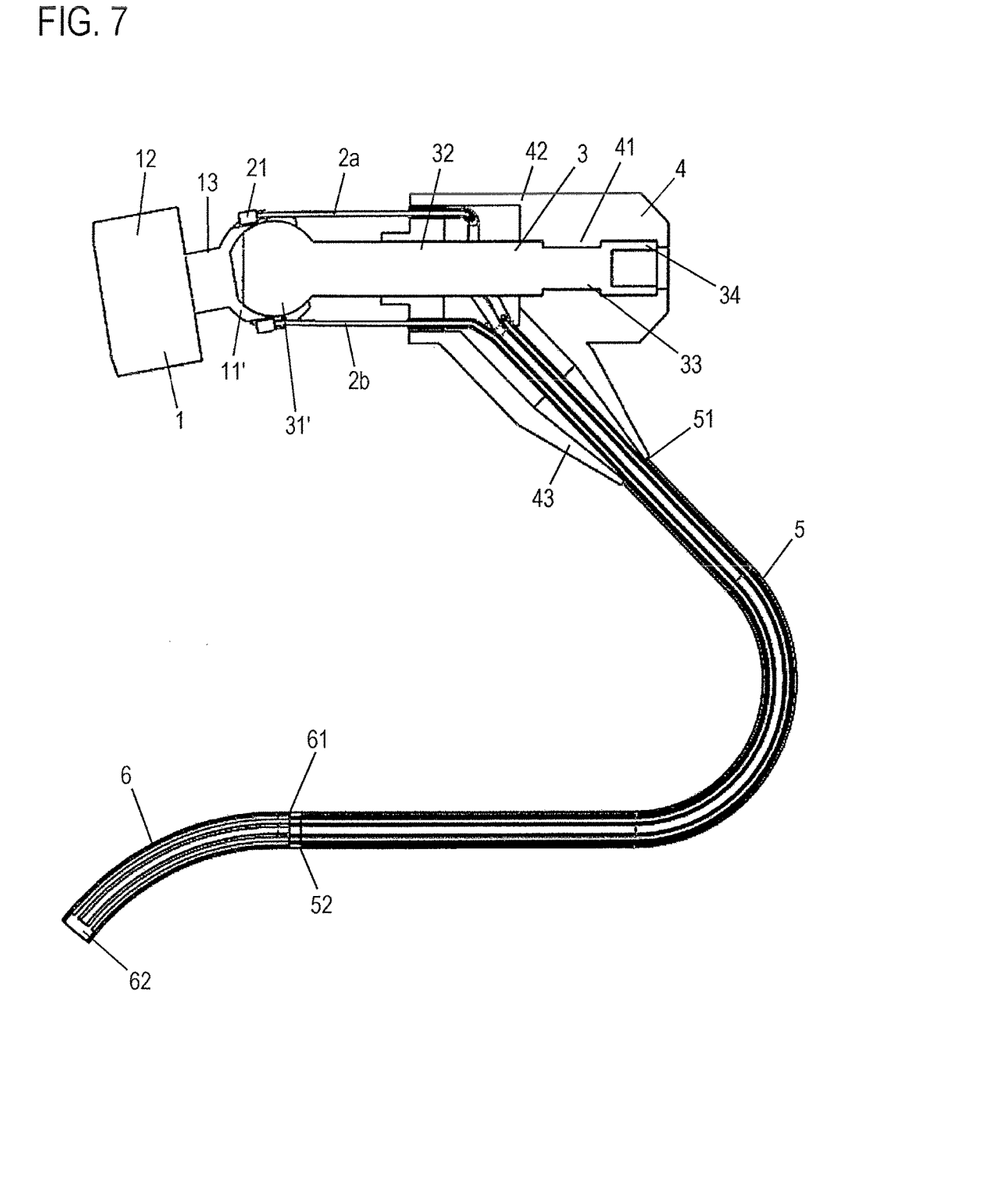
FIG. 7 shows a schematic sectional view of the deflection movement transmission device of the second embodiment when deflected to the left.
Figure 8:
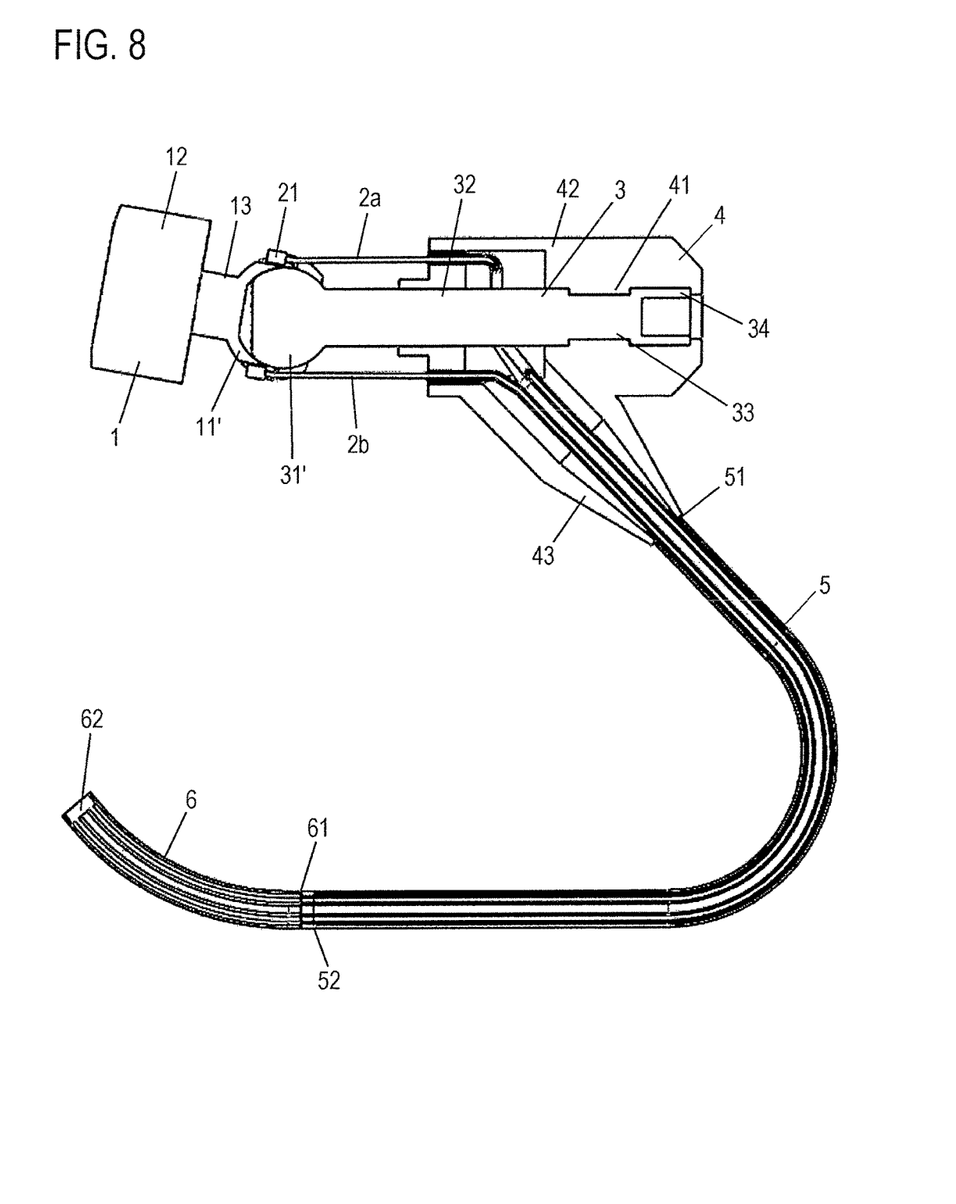
FIG. 8 shows a schematic sectional view of the deflection movement transmission device of the second embodiment when deflected to the right.

The control element 1 consists of a cylindrical element with a control head 12 on the bottom side of which a shaft portion 13 is centrically arranged; other than in the previous embodiment the same turns into a hollow ball portion 11' on whose outer surface the wire bodies 2 are anchored. The hollow ball portion 11' is open at its side facing away from the head 12. In particular, the opening at the hollow ball portion 11', for example, is designed such that the hollow ball portion 11' constitutes about 9/10 of a ball from which about 1/10 is cut off.

The control element 1 is rotationally symmetrical, as it is shown in FIGS. 6-8. The control element 1 is made of a plastic material but may also be made of metal.

Thus, the control element 1 is seated as a joystick on a head 31 of the rod element 3. In particular, the hollow ball portion 11' of the control element 1 is seated on a counter-ball portion 31' which, in this embodiment, forms the head of the rod element 3. The counter-ball portion 31' is formed in such a way that it has a ball shape of such a size that the hollow ball portion 31' seated thereon is smoothly movable. The dimensional relations between the counter-ball portion 31' and the hollow ball portion 11' are of such a nature that a relative movement of the control element 1 to the rod element 3 is possible without any big effort by the operator and, on the other hand, the hollow ball portion 11' is not seated loosely on the counter-ball portion 31'.

The rod element 3 has a longitudinal cylinder 32 which, at its proximal side, turns into the counter-ball portion 31' and, at its distal end portion, a screw end 34 which is, for example, designed as an inner square. Distal to the square end 34, the rod element 3 has an outer threaded portion 33 at its outer cylinder surface. The rod element 3 is constructed rotationally symmetrical. The counter-ball portion 31', the longitudinal cylinder 32 and the square end 34 are configured as an integral rod element. The longitudinal cylinder 32 of the rod element 3 is formed as a cylinder with a smooth outer surface, except for the threaded portion 33 provided thereon.

As it is shown in FIGS. 6-8, the rod element 3 is seated in a rod element holder 4. As in the first embodiment, the rod element holder 4 consists of a cylinder element 42 that is constructed rotationally symmetrical and has a centric inner channel. The cylinder element 42 has the hollow space facing towards the control element 1 and a bottom on the side of the rod element holder 4 facing away from the control element 1. The bottom of the rod element holder 4 has the concentric inner channel. An inner thread 41 is provided in the concentric inner channel. As it is schematically indicated in the Figures, the outer thread 33 of the rod element 3 is seated on the inner thread 41 of the rod element holder 4, wherein, by means of a screwing movement, the rod element 3 can be concentrically screwed in or out relative to the rod element holder 4. For the purpose of effecting the screwing movement, an appropriate tool is inserted into the square end 34 of the rod element 3.

The cylinder element 42 of the rod element holder 4 has a catheter connecting element 43 at its outer circumferential surface. Also in the present embodiment, the catheter connecting element 43 extends in an acute angle relative to the cylinder element 42 of the rod element 4, as it becomes apparent from the drawings.

The catheter connecting element 43 is designed as a round hollow profile which forms a channel branch from the distal hollow space of the cylinder element 42. The catheter connecting element 43 is formed cylindrically and tapers in the direction facing away from the cylinder element 42. On the inside, the catheter connecting element 43 has a concentric channel for guiding the wire bodies 2. At its distal end, the catheter connecting element 43 has a circular port.

The catheter tube 5 is attached to the circular port of the catheter connecting element 43. In particular, the proximal end 51 of the catheter tube 5 is seated on the port of the catheter connecting element 43. At its distal end, the catheter tube has a ring 52 accommodated therein. The ring 52 forms the distal end of the catheter tube and the transition to the deflecting portion 6.

The deflecting portion 6 is a bendable body made of an elastic material in a known manner. At its proximal end, the deflecting portion has a deflecting connection 61 at which it is connected to the ring 52 of the catheter tube 5. At the distal end, the deflecting portion has a deflecting cap 62, on which a camera, a laser and/or a camera, etc. are arranged. Further functional units can be integrated at the deflecting cap 62.

Figure 9:
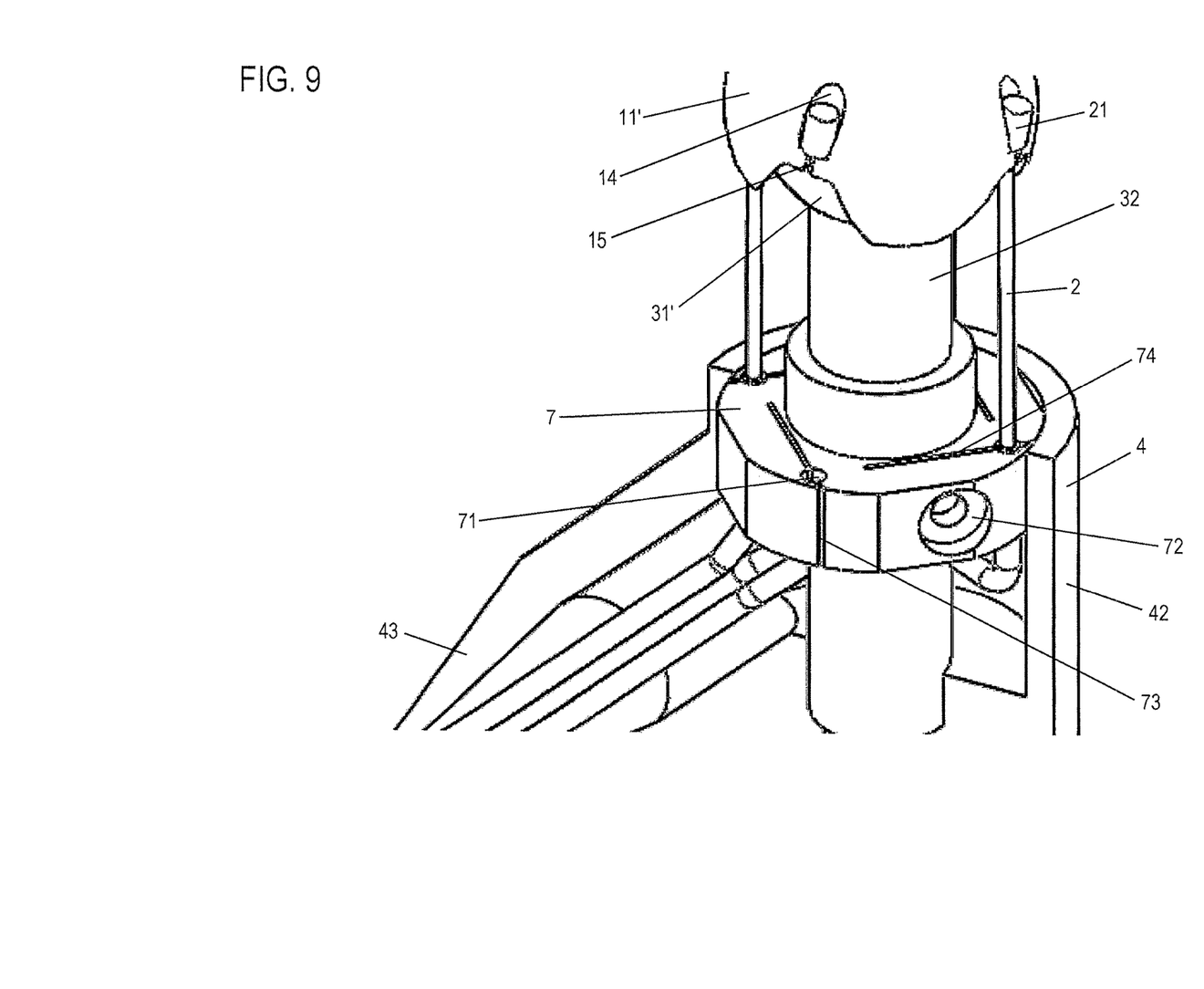
FIG. 9, in a schematic, partial representation in perspective, shows details of the connection of the wire bodies to the control element of the second embodiment and how the wire bodies are guided to the catheter tube.

FIG. 9 shows in a schematic, partial representation in perspective details of the connection of the wire bodies to the control element of the second embodiment and how the wire bodies are guided to the catheter tube. For reasons of better clarity, the front left wire body 2 is not represented in this Figure.

As it is shown in FIG. 9, several hang-in cavities 14 are provided on the outer circumferential surface of the hollow ball portion 11' on the equatorial line of the hollow ball portion 11'. In the present embodiment, four hang-in cavities 14 are provided on the equator of the hollow ball portion 11'. In particular, the hang-in cavities 14 are recesses formed in the hollow ball portion 11' which have a circular cross section and a bottom, wherein the bottom extends approximately perpendicular to an extension direction of the hang-in cavity 14, and is located at the equatorial line, more specifically, perpendicular to the equator of the hollow ball portion 11'. When producing the hang-in cavity 14, the hollow ball portion 11' can be produced from the proximal side, for example by milling, so that the hang-in cavity is formed as a laterally open blind hole on the outer circumferential surface of the hollow ball portion 11'. Any other production methods are possible. The outer diameter of the hang-in cavity 14 is chosen such that a barrel nipple 21 of the wire body 2 fits into the hang-in cavity 14. On the bottom of the hang-in cavity 14, i.e. at the distal end of the hang-in cavity 14, a channel 15 is designed as wire body hang-in, the channel extending coaxially to the longitudinal extension of the control element 1 and having a diameter greater than the outer diameter of the wire body 2, but smaller than the outer diameter of the barrel nipple 21 of the wire 2. In other words, the hang-in cavity 14 and the wire body hang-in 15 are similar as in the first embodiment.

The number of wire bodies 2 is not limited here, either. Should two or more wire bodies 2 be provided, the corresponding hang-in cavities 14 are arranged at the equator of the hollow ball portion 11' equally spaced apart from each other.

As in the first embodiment, a wire body guiding ring 7 having the same number of tangential slits 74 as there are wire guides 2, is provided as is shown in FIG. 9. Wire guide openings 71 extending coaxially to the common axes of the rod element 3 and the cylinder element 42 of the rod element holder 4 are drilled into the slits 74.

The slit end 73 of each tangential slit 74 is located at the outer circumferential surface of the flat wire guiding ring 7, as it is shown in FIG. 9. As in the first embodiment, the outer circumferential surface of the flat wire guiding ring 7 is provided with a threaded hole 72 that accommodates a fixing screw by means of which the wire guiding ring 7 is fixed to the cylinder element 42 of the rod element holder 4. Although only one threaded hole 72 for a fixing screw is shown in FIG. 9, also plural threaded holes 72 for a corresponding number of plural fixing screws can be provided on the wire guiding ring 7.

Also in this case, the wire bodies 2 are guided through the catheter tube 5 and through the ring 52 of the catheter tube and are anchored at the deflecting cap 62 of the deflecting portion 6. The wire bodies 2 are anchored at the deflecting cap 62 in such a way that they are attached in a manner equally spaced apart from each other and in the same order as on the hollow ball portion 11'. The ring 52 has openings for the wire bodies 2 in a manner corresponding to the design of the wire guiding ring 7.

Mode of Operation

As in the first embodiment, the control element 1 can be operated as a joystick. In this embodiment, the hollow ball portion 11' can be moved on the counter-ball portion 31' of the rod element 3. Thereby, a pivoting operation of the joystick 1 relative to the rod element 3 in any direction is possible. The direction and the extent of the deflection movement of the joystick 1 relative to the rod element 3 is then transmitted by the wire bodies 2 arranged on the deflecting cap 62 to the deflecting portion 6 designed as bendable body. In other words, if the joystick 1 is moved to the left relative to the rod element 3, the deflecting portion performs a movement directed to the left, as is shown in FIG. 7. If the joystick 1 is moved to the right relative to the rod element 3, the deflecting portion performs a movement directed to the right, as it is shown in FIG. 8.

Alternatives

The wire body 2 is hung into the hang-in cavity 14, which is shown in FIG. 4, in the form of a barrel nipple 21. The invention is not restricted to a barrel nipple and the nipple 21 can be designed as a known pear nipple; any similar nipples can be used. The shape of the hang-in cavity 14 can be adapted to the chosen shape of the nipple.

In the first embodiment, the foot surface 11A is curved outwardly. Further, the front face 31A of the head portion 31 is curved outwardly. The invention is not restricted thereto. By using the principle of the invention, the deflection movement transmission device can also be configured such that the foot surface 11A is designed planar and the front face 31A is curved outwardly. On the other hand, the deflection movement transmission device can also be configured such that the foot surface 11A is curved outwardly and the front face 31A is designed planar. A construction in which the front face 31A is curved inwardly and the foot surface 11A is curved outwardly is also possible, as long as the curvature radius of the front face 31A is greater than the curvature radius of the foot surface 11A. In a similar manner, the front face 31A can be curved outwardly and the foot surface 11A can be curved inwardly, as long as the curvature radius of the front face 31A is smaller than the curvature radius of the foot surface 11A. It is merely sufficient that the foot surface 11A can roll on the front face 31A safely and in a controlled manner.

In the second embodiment, the size of the hollow ball portion 11' has been chosen such that it constitutes ⁹⁄₁₀ of a ball. The invention is not restricted thereto. Any hollow ball shape size of the hollow ball portion 11' can be chosen, as long as the same can still perform the pivotal movement on the counter-ball portion 31'. The hollow ball portion 11' can also have a shape of a hollow ball ring portion that extends by a predetermined minimum amount parallel to the axial direction of the control element 1 to both sides of the equatorial line and basically forms an equatorial band.

The square end 34 serves to enable a screwing movement in order to perform a relative movement of the rod element 3 to the rod element holder 4 at the threaded portions 33 and 41. The invention is not restricted to the square shape at the end 34 of the rod element 3. A triangular shape, octagonal shape or another polygonal shape can be chosen. Basically, any shape that enables application of a torque generating the rotational movement of the rod element at the end 34 can be chosen.

In the embodiments, the relative movement of the rod element 3 to the rod element holder 4 is effected by the threaded portions 33 and 41. By the movement of the rod element 3 relative to the rod element holder 4, the wire bodies 2 are tensioned. Any other way of movement of the rod element 3 to the rod element holder 4 can be chosen for this purpose. For example, the rod element holder 4 can have a continuous inner cylinder hole and the rod element 3 can have a continuous cylindrical longitudinal cylinder 32, wherein a pulling device is attached to the end 34 of the rod element 3. In the rod element holder 4, a threaded hole can be provided perpendicular to the axis of the rod element holder; a locking screw adapted to lock the longitudinal cylinder 32 in any position relative to the rod element holder is seated therein.

In the embodiments, the catheter connecting element 43 extends in an acute angle, under consideration of FIG. 1, to the rod element holder 4. The invention is not restricted thereto. Any extension angle of the catheter connecting element 43 to the rod element holder 4 can be chosen.

In the embodiments, the catheter tube 5 is a transmission guiding body having a hollow space, in which the movement transmission wire body is guided. During a pivotal movement of the control element, the movement transmission wire bodies 2 are subject to pulling forces and pushing forces. When these pulling forces and pushing forces are exerted on them, the movement transmission wire bodies 2 must be adapted to slide on the transmission guiding body. The transmission guiding body can have a closed cross section, as it is the case for a catheter tube 5. The invention is not restricted thereto. The transmission guiding body can be a rail element or a box element, on which the movement transmission wire body is guided. The cross section of the transmission guiding body can be open on the side on which the movement transmission wire bodies 2 do not slide.

The control element 1 can be lockable in order to lock a deflected position of the control element 1. In the second embodiment, the locking takes place by a locking screw which, for example, penetrates the hollow ball portion 11' and engages at the surface of the counter-ball portion 31' and, thus, acts as a friction brake in such a way that a particular deflected position of the control element 1, hence, of the control lever, is lockable by a friction brake. Moreover, a locking can take place in all embodiments by clamping the movement transmission wire body/bodies 2, for example at the wire guiding ring 7 or at the cylinder element 42 of the rod element holder 4. In case all wires 2 are locked, for example by a locking clamp attached to the wire guiding ring 7 or the cylinder element 42, a safe locking of a deflected position of the control element 1 is thereby achieved. Other technical possibilities for blocking the wires 2 can be chosen.

In the embodiments, the deflection movement transmission device is applied to an endoscope deflecting control in an endoscope. The deflection movement transmission device can also be applied in other technical fields. A use in water-conducting channels, mining tunnels, etc. is possible. The invention can be applied anywhere, where pivotal movements are converted into deflection movements of a deflection element.

LIST OF REFERENCE SIGNS 1 control element; joystick
2, 2a, 2b wire body
3 base element; rod element
4 rod element holder
5 catheter tube
6 bendable body, deflecting portion
7 wire guiding ring
11 pivot portion
11A foot surface of the pivot portion 11
11' hollow ball portion
12 head of the control element 1
13 shaft portion
14 hang-in cavity
15 wire body hang-in
21 barrel nipple
31 head portion
31A front face of the head portion 31
31' counter-ball portion
32 longitudinal cylinder
33 threaded portion of the rod element 3
34 square end; distal end of the rod element 3
41 threaded portion of the rod element holder 4
42 cylinder element
43 catheter connecting element
51 catheter tube connection
52 ring
61 deflecting connection
62 deflecting cap
71 wire guiding bore
72 threaded hole for a fixing screw
73 slit inlet
74 tangential slit

The invention claimed is:

1. A deflection movement transmission device comprising:
a base element having a head portion,
a control element for effecting a deflection movement, the control element having a pivot portion that is supported on the head portion of the base element and is pivotable relative to the head portion of the base element for effecting a deflection movement,
at least one movement transmission wire body that is connected to the pivot portion of the control element,
an elongate transmission guiding body having a distal connector and a distal end, wherein the movement transmission wire body is guided along the elongate transmission guiding body,
a bendable body to be deflected that is seated at the distal end of the transmission guiding body, opposite to the control element, and to which the movement transmission wire body is mounted in a manner spaced apart from the connector to the transmission guiding body,
the control element being configured as an actuating lever which, at the pivot portion, has a foot surface facing the base body,
the head portion of the base element having a front face facing the control element,
the foot surface of the pivot portion of the control element and the front face of the head portion of the base element being respectively curved towards each other so that the foot surface and the front face can be rolled on each other,
the pivot portion of the control element having an articulation point of the movement transmission wire body at its outer side.

2. The deflection movement transmission device according to claim 1, wherein the head portion is integrally connected to the base element at a side facing away from the control element, the base element comprising a rod element that is axially movable in a rod element holder from which the transmission guiding body extends, so as to tension the movement transmission wire body.

3. The deflection movement transmission device according to claim 2, wherein the rod element has a longitudinal axis and the transmission guiding body extends from the longitudinal axis of the rod element at a predetermined angle at the side of the rod element holder.

4. The deflection movement transmission device according to claim 1, wherein a first end of the movement transmission wire body is connected to the control element and an opposite second end of the movement transmission wire body is fixed to the distal end portion of the body to be deflected.

5. The deflection movement transmission device according to claim 1, wherein the transmission guiding body has a hollow space in which the movement transmission wire body is guided.

6. The deflection movement transmission device according to claim 1, wherein the control element is lockable so as to lock a deflected position of the control element.

7. The deflection movement transmission device according to claim 6, further comprising a fiction brake wherein the control element functions as a deflectable joystick whose deflected position is lockable by the friction brake.

8. The deflection movement transmission device according to claim 1, wherein one or more movement transmission wire bodies are provided, the first ends of which are equally spaced apart from each other and equatorially articulated to the control element, and the opposite second ends of which are fixed to the distal end portion of the body to be deflected in a corresponding manner equally spaced apart from each other.

9. An endoscope comprising the deflection movement transmission device according to claim 1, wherein the transmission guiding body is a catheter tube and the body to be deflected is a bending portion.

* * * * *